Figure 1:
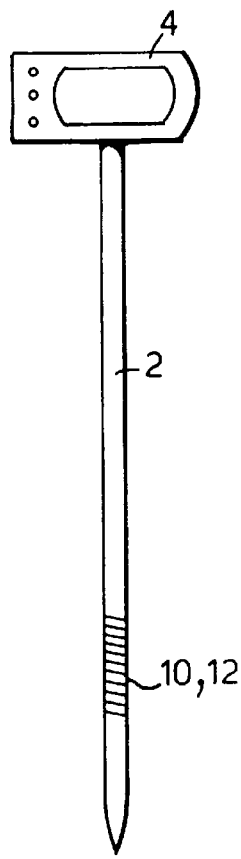

United States Patent
Dadachanji et al.

[11] Patent Number: 6,076,396
[45] Date of Patent: Jun. 20, 2000

[54] MOISTURE SENSING PROBE

[75] Inventors: Fali Minocher Dadachanji, Marlow; John Standfield, High Wycombe, both of United Kingdom

[73] Assignee: Protimeter plc, United Kingdom

[21] Appl. No.: 09/255,304

[22] Filed: Feb. 22, 1999

[30] Foreign Application Priority Data

Feb. 20, 1998 [GB] United Kingdom .................... 9803638

[51] Int. Cl.⁷ .............................. G01N 5/02; G01N 25/56
[52] U.S. Cl. .................................................................. 73/73
[58] Field of Search ............................... 73/73; 324/694, 324/696

[56] References Cited

U.S. PATENT DOCUMENTS

| | | | |
|---|---|---|---|
| 2,793,527 | 5/1957 | Turner, Jr. et al. | 73/73 |
| 3,968,428 | 7/1976 | Numoto | 324/694 |
| 4,044,607 | 8/1977 | Deal . | |
| 4,069,716 | 1/1978 | Vanasco et al. | 73/73 |
| 4,399,404 | 8/1983 | Resh | 73/73 |
| 4,445,788 | 5/1984 | Twersky et al. | 73/73 |
| 4,514,722 | 4/1985 | Batcheler et al. . | |
| 4,654,598 | 3/1987 | Arulanandan et al. . | |
| 4,845,978 | 7/1989 | Whitford | 73/73 |
| 5,442,293 | 8/1995 | Lange | 324/696 |

FOREIGN PATENT DOCUMENTS

| | | |
|---|---|---|
| 0 216 474 | 4/1987 | European Pat. Off. . |
| 0 759550 | 2/1997 | European Pat. Off. . |
| 1102740 | 8/1965 | United Kingdom . |
| 1419235 | 3/1974 | United Kingdom . |
| 2210693 | 10/1988 | United Kingdom . |
| 2222683 | 2/1989 | United Kingdom . |
| WO97/04305 | 2/1997 | WIPO . |

*Primary Examiner*—William Oen
*Attorney, Agent, or Firm*—David E. Rogers; Michael A. Lechter; Squire, Sanders & Dempsey

[57] ABSTRACT

A probe for use in sensing moisture content of bulk grain or other granular material comprises a cylindrical tube, for example of plastics, having a tapering nose, and having adjacent said nose first and second electrical conductors wound helically around the tube so that the turns of one conductor are spaced from, and alternate with, the turns of the other conductor. The conductors are electrically insulated from one another by the plastics tube but are exposed on the surface of the tube, or project slightly from such surface, for direct electrical contact with the granular material. The conductors extend through respective apertures in the plastics tube and are connected within the tube to respective insulated conductors extending to electronic measuring circuitry within a handle of the probe.

9 Claims, 1 Drawing Sheet

U.S. Patent     Jun. 20, 2000     6,076,396

MOISTURE SENSING PROBE

This invention relates to apparatus for measuring the moisture content of granular material in bulk.

It is known to measure the moisture content of granular material, such as cereal grain, in bulk, using elongate probes which carry electrodes. In use, such a probe is inserted into a heap of grain, for example, so that the electrodes are buried in the heap and the moisture content of the heaped grain is assessed by measuring the impedance, e.g. resistance and/or capacitance, between the electrodes, the impedance measured being a function of the moisture content of the grain.

Currently available moisture-sensing probes of this type have protruding electrodes, which hinder the ready insertion of the probes into bulk grain.

It is an object of the present invention to provide an improved sensing device for use in measuring the moisture content of cereal grain or other granular material and which can be inserted more readily into the bulk granular material than known sensing devices.

According to the present invention there is a provided a sensing device for use in measuring the moisture content of cereal grain or other granular material, comprising an elongate probe for insertion in the bulk granular material, said probe having a lateral surface incorporating mutually insulating electrodes on said surface.

Figure 2:
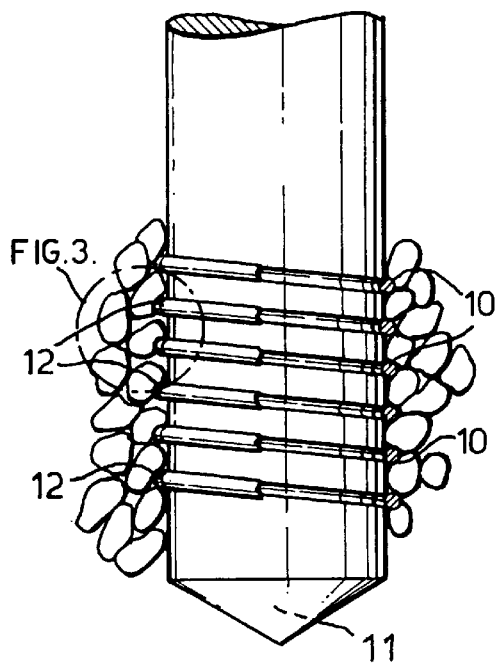
Figure 3:
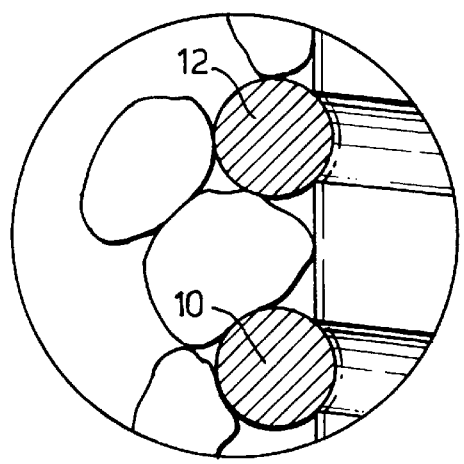

An embodiment of the invention is described below with reference to the accompanying drawings, in which:

FIG. 1 is a side elevation view of a moisture sensing probe embodying the invention, FIG. 2 is a fragmentary side elevation view, to an enlarged scale as compared with FIG. 1, of a portion of the probe of FIG. 1, with schematic representations of grains, adjoining the probe, in a heap of such grain in which the probe may be supposed to be inserted and FIG. 3 is a view to a still larger scale of the region encircled in FIG. 2.

Referring to the drawings, reference 2 in FIG. 1 indicates an elongate cylindrical probe 2, for example of tough plastics tubing, which, at its lower end, terminates in a tapered nose for ease of insertion of the probe, longitudinally, into a body of bulk granular material, for example, a heap of cereal grain. The probe may have, as illustrated, a handle 4 at its opposite end. Adjacent its tapered lower end, the probe has, wound helically around the probe, first and second electrical conductors forming electrodes 10, 12, respectively which, in the arrangement illustrated, are so arranged that turns of electrodes 10 and 12 are arranged alternately along the respective portion of the length of the probe 2. The electrodes 10, 12, are electrically insulated from one another and each may, at one end of the electrode winding, extend through a respective aperture, (not shown) into the hollow interior of the probe 2, being connected, within the probe, to a respective insulated conductor extending to electronic metering circuitry (not shown) mounted within the handle structure 4, if the probe is self-contained, or to a flexible cable (not shown) extending to a separate housing (not shown) accommodating such circuitry.

The humidity sensor may be arranged to operate by measuring the impedance, between the electrodes 10, 12, when the latter are supplied with a high frequency alternating voltage signal and in this case the electrodes 10, 12, may have an insulating coating of plastics insulating the electrodes from the body of the probe 2. Alternately, and preferably, the probe 2 may be of insulating material, such as a tough plastics, in which case the electrodes need not be and preferably are not insulated.

Preferably, as illustrated in FIG. 1, the two separate electrodes 10, 12, spirally wound on the tubular body of the probe are so arranged that the electrodes stand proud of the surface of the probe body, thus affording a ribbed effect as shown in FIGS. 1 and 3. If the probe is intended to measure pure electrical resistance of grain, the conductors forming electrodes 10 and 12 may simply be bare, round-section metal wire located in shallow helical channels or grooves extending around the probe body so that, in section, as viewed in FIG. 3, the major part of each conductor projects radially outwardly from the circumference of the generally cylindrical probe body If the probe is intended to measure impedance of the grain at relatively high electrical frequencies, each electrode 10, 12 may have a tin layer of protective insulation, not shown, thereon.

When the probe illustrated is inserted into a heap of grain and turned slightly the spirally wound electrodes projecting from the probe like ribs allow the grain to settle preferentially in the spaces between the electrodes and hence the number of grains randomly distributed around the electrodes is slightly lessened and the number of grains correctly spaced between the electrodes increases. This allows for very much improved measurement of the impedance of the grain surrounding the stem.

A number of parameters can be changed to good effect to optimise the probe for use in different grains, for example:

1. The spacing between the electrodes 10 and 12 can be increased for grain of larger grain size, such as maize and decreased for smaller seeds such as rape seed. By way of example such spacing may be 7 mm for use in bulk maize, 4 mm for use in wheat and 2 mm for use in rape seed.
2. The diameter or cross-sectional shape of the electrode material can be changed to produce a more or less pronounced ribbed effect. Thus, for example, the electrodes may be formed of wire of square or triangular section instead of round-section wire.
3. The axial length of the region of the probe over which the spirally wound electrodes extend can be changed to increase or decrease the signal strength and the size of the grain sample measured.
4. The measurement of moisture from the electrodes can be effected by a number of methods using signals of varying frequencies and voltage. The best conditions for sensing and measuring moisture content in different granular materials can be determined experimentally. Suitable circuitry (not shown) can be arranged to excite the electrodes.

A separate temperature measuring sensor, or temperature sensing element 11 can also be embedded into the tip of the stem whereby the instrument is made capable of measuring temperature and moisture content of grain to be measured, and displayed on an appropriate display, at the same time.

The circuitry connected with the electrodes 10, 12, may include appropriate analog or digital computing means and may be arranged to drive an appropriate display and for to store the measured values for future reference. Such circuitry and display may, for example, be carried by the handle of the probe, or alternatively may be provided in or on a remote console to which the probe is connected by flexible cable (not shown), as discussed above.

Whilst, conveniently, the electrodes 10, 11, may be formed as elongate conductors wound helically around the probe, they may, alternatively, take the form of distinct annular rings encircling the probe, or even of longitudinally extending ribs or bars on the exterior of the probe, bonded or otherwise secured to the probe.

What is claimed is:

1. A sensing device for use in measuring the moisture content of cereal, grain or other bulk granular material, said device comprising an elongate probe for insertion in the bulk granular material, said probe having a first end and a second end, and including a handle at the first end and a tapered nose at the second end, said probe having a lateral surface incorporating mutually insulating electrodes on said surface, wherein at least one of the electrodes extends outward from said lateral surface of the probe.

2. A sensing device according to claim 1 wherein each of the electrodes extends outward from the lateral surface of the probe.

3. A sensing device according to claim 1 wherein said probe also incorporates a temperature sensing element.

4. A sensing device according to claim 1 wherein the probe comprises an elongate cylindrical body of insulating material and at least one of the electrodes comprises an annular band extending around the probe.

5. A sensing device according to claim 1 wherein the probe comprises an elongate cylindrical body of insulting material and at least one of the electrodes comprises a helical coil extending around the probe.

6. A sensing device according to claim 5 wherein there are two electrodes, each of the electrodes being formed as a helical coil, the electrodes being so arranged on the probe that respective turns of the electrodes are arranged alternatively along the length of the probe wherein the spacing between the respective electrodes is 2 to 7 mm.

7. The sensing device of claim 1 wherein the electrodes are formed of wire having a round cross section.

8. The sensing device of claim 1 wherein the electrodes are formed of wire having a square cross section.

9. The sensing device of claim 1 wherein the electrodes are formed of wire having a triangular cross section.

* * * * *